United States Patent [19]
Baran

[11] Patent Number: 5,025,797
[45] Date of Patent: Jun. 25, 1991

[54] AUTOMATED BIOPSY INSTRUMENT

[76] Inventor: Gregory W. Baran, 18878 Greenwood Ct., Spring Lake, Mich. 49456

[21] Appl. No.: 330,230

[22] Filed: Mar. 29, 1989

[51] Int. Cl.$^5$ .............................................. A61B 10/00
[52] U.S. Cl. ..................................... 128/754; 606/171
[58] Field of Search ........ 128/305, 310, 749, 751–755; 604/21, 22, 51, 164, 165, 166, 264; 606/167, 170, 171

[56] References Cited

U.S. PATENT DOCUMENTS

| | | | |
|---|---|---|---|
| 2,496,111 | 1/1950 | Turkel . | |
| 3,256,874 | 6/1966 | De Marco | 128/751 |
| 3,342,175 | 9/1967 | Bulloch | 128/754 |
| 3,353,531 | 11/1967 | Armao | 128/751 |
| 3,391,690 | 7/1968 | Armao | 128/751 |
| 3,394,699 | 7/1968 | Koett | 128/759 |
| 3,452,741 | 7/1969 | Schaffer | 128/755 |
| 3,477,423 | 11/1969 | Griffith | 128/754 |
| 3,561,429 | 2/1971 | Jewett | 128/752 |
| 3,608,539 | 9/1971 | Miller | 128/314 |
| 3,630,192 | 12/1971 | Jamshidi | 128/310 |
| 4,396,021 | 8/1983 | Baumgartner | 128/754 |
| 4,600,014 | 7/1986 | Beraha | 128/754 |
| 4,667,684 | 5/1987 | Leigh | 128/754 |
| 4,681,103 | 7/1987 | Boner et al. | 128/662.05 |
| 4,699,154 | 10/1987 | Lindgren | 128/754 |
| 4,735,215 | 4/1988 | Goto et al. | 128/754 |
| 4,776,346 | 10/1988 | Beraha et al. | 128/754 |
| 4,781,202 | 11/1988 | Janese | 128/754 |
| 4,791,371 | 12/1988 | Krol | 128/653 SC |
| 4,817,631 | 4/1989 | Schnepp-Pesch et al. | 128/753 |
| 4,881,551 | 11/1989 | Taylor | 128/754 |
| 4,893,635 | 1/1990 | deGroot et al. | 128/654 |
| 4,924,878 | 5/1990 | Nottke | 128/751 |

FOREIGN PATENT DOCUMENTS

| | | | |
|---|---|---|---|
| 0010321 | 4/1980 | European Pat. Off. | 128/754 |
| 0173653 | 3/1986 | European Pat. Off. . | |
| 0325426 | 7/1989 | European Pat. Off. . | |
| 8802580 | 9/1988 | Fed. Rep. of Germany . | |

OTHER PUBLICATIONS

Abstract-Soc. of Magnetic Resonance in Medicine, Aug. 22, 1986, vol. 4, pp. 1329–1330.
Roth Biopsy Needle, Cook Urological Inc., Spender, Ind. 47460, 1986.

*Primary Examiner*—Randy Citrin Shay
*Attorney, Agent, or Firm*—Varnum, Riddering, Schmidt & Howlett

[57] ABSTRACT

The invention is for a biopsy instrument having a stationary shaft secured to which is a stylet such that, once secured, the stylet does not move relative to the instrument. The stylet is telescopically received by a cannula which is mounted to a spring-loaded guide; the cannula and the guide move between charged and discharged positions. Also provided is a safety cap, which travels within slots formed in opposite sides of the cylindrical casing that houses the shaft, the guide and the spring. Retracting the safety cap moves the guide and the cannula from the discharged to the charged position where a release lever engages the guide. The safety cap covers the release lever to prevent accidental actuation of the instrument. The instrument is fired by sliding the safety cap forward and depressing the exposed release lever, which allows the spring to drive the cannula forward, toward the discharged position and over the stationary stylet, so that a tissue sample may be taken.

11 Claims, 7 Drawing Sheets

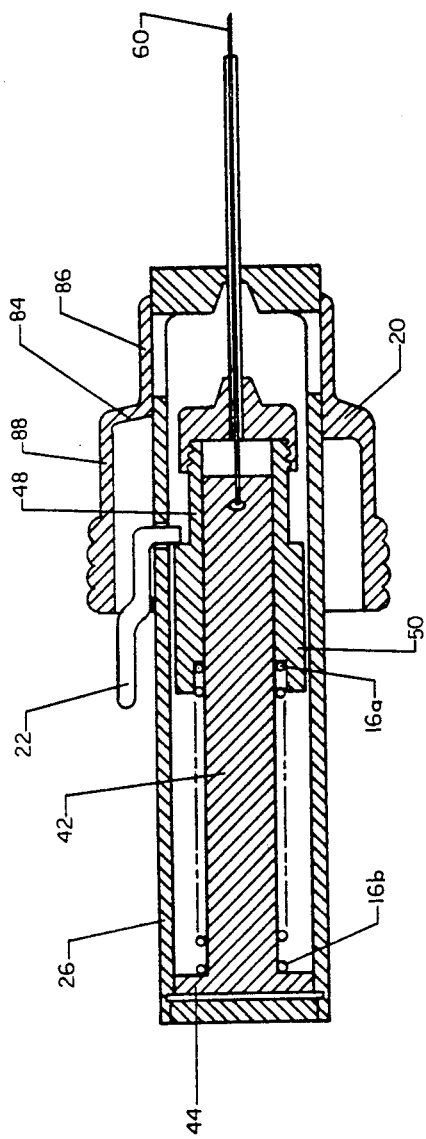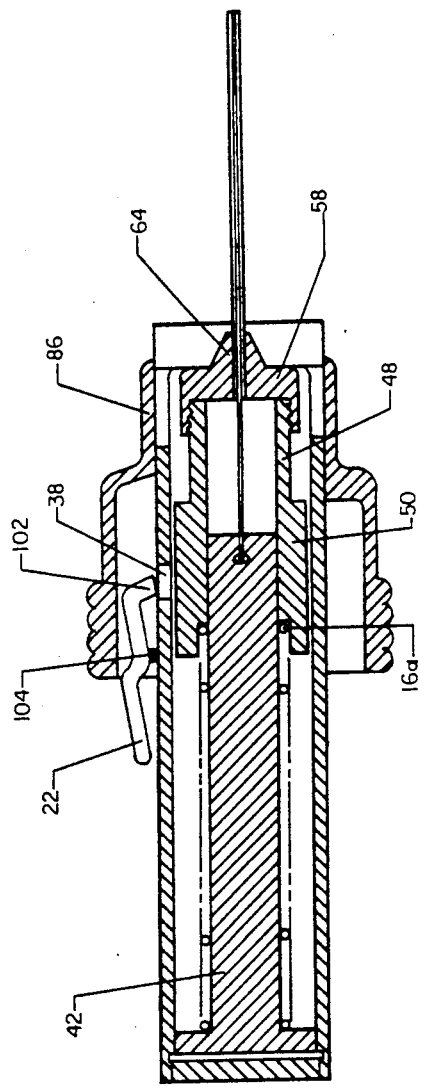
FIG. 4
FIG. 4A

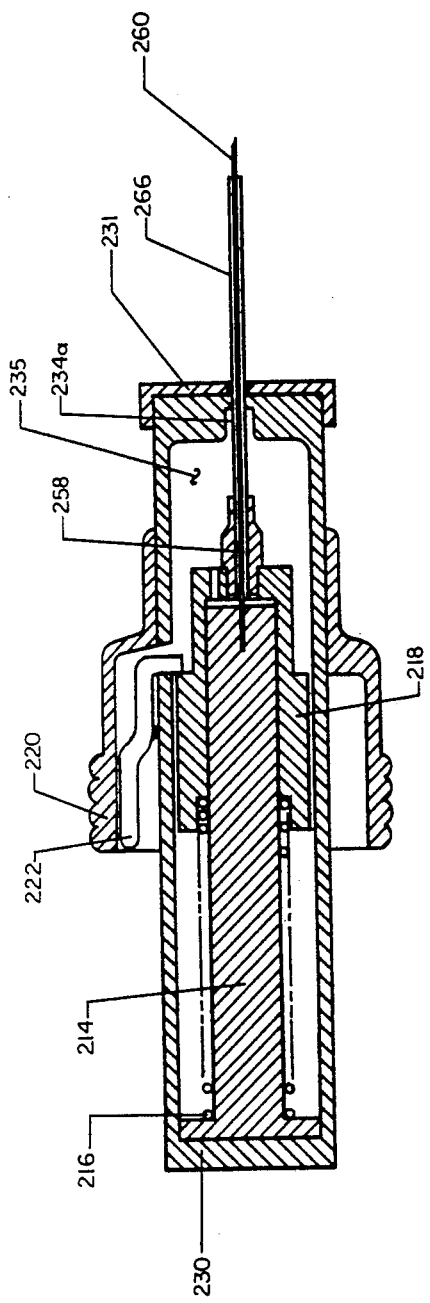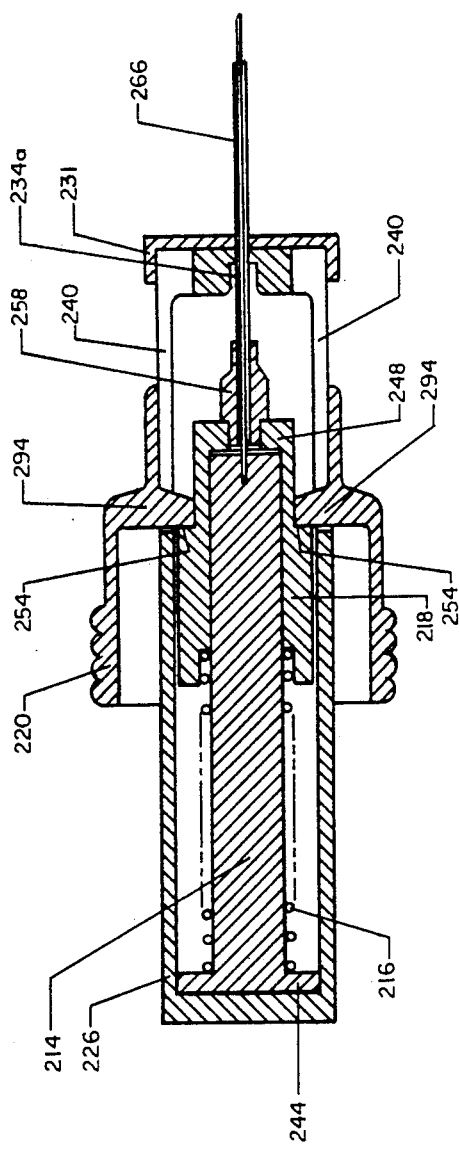

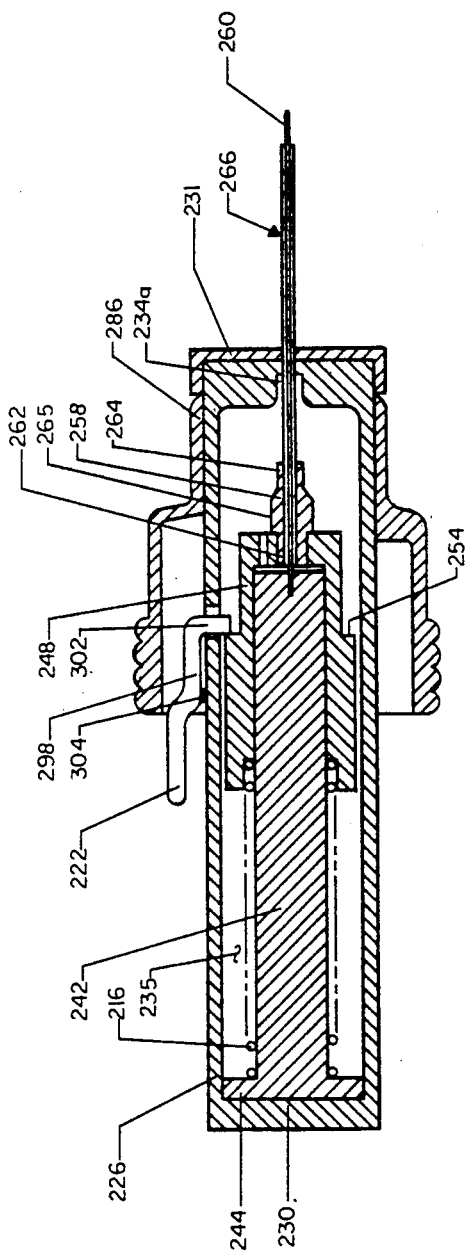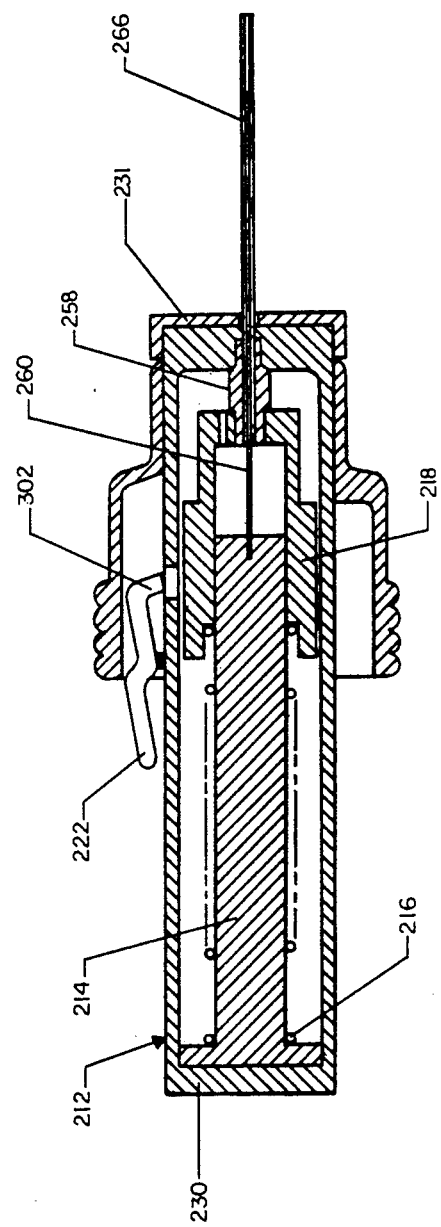

AUTOMATED BIOPSY INSTRUMENT

BACKGROUND OF THE INVENTION

1. Field of the Invention

This invention relates generally to a biopsy instrument; viz., a device for removing a sample of tissue from a human being or an animal. More particularly, the invention relates to an automated biopsy instrument in which a spring-loaded outer cannula is driven over an inner stationary stylet to obtain the tissue sample.

2. Description of the Related Art

The procedure known as biopsy, or the removal of samples of human and animal internal tissue, has been for many years a favored method for the nonsurgical diagnosis of tissue. Traditionally, biopsy has been performed in a two-step manual technique employing a needle in which an outer hollow cutting cannula telescopically receives an inner stylet which is slidable between retracted and extended positions relative to the cannula. In performing the first step of the technique, the physician places the tip of the needle (with the stylet retracted inside the cannula) against the tissue mass to be sampled and manually drives the stylet forward into the tissue mass. In a typical instrument of this type, the stylet extends rearwardly therefrom and is fitted with a push-knob to facilitate the driving of the stylet in the forward direction. To carry out the second step, the physician manually drives the cutting cannula forwardly over the stylet, thereby severing a tissue sample and retaining it within the cannula's hollow interior.

Examples of manually operated biopsy needles of this general type are disclosed in U.S. Pat. No. 4,600,014, issued July 15, 1986 to D. Beraha for "Transrectal Prostate Biopsy Device and Method", and U.S. Pat. No. 3,477,423, issued Nov. 11, 1969 to L. K. Griffith for "Biopsy Instrument".

Such manually operated two-step devices are awkward to manipulate, and the tissue samples obtained may often be unsatisfactory. The depths to which the stylet and the cannula are driven into the tissue mass must be carefully controlled for accuracy and efficiency. Caution is required, as well, in applying the force with which the stylet and cannula are plunged forward. Too little force may not sever the tissue sample from the mass; too much force may cause unnecessary damage to the surrounding vital tissues.

In an effort to remedy these problems, various automated devices have been developed. For example, U.S. Pat. No. 3,452,741, issued July 1, 1969 to R. C. Schaffer for "Conetome", discloses an instrument for performing cervical biopsies in which an electric motor imparts reciprocating movement to a pair of serrated scalpel blades.

U.S. Pat. No. 4,667,684, issued May 26, 1987 to H. G. Leigh for "Biopsy Device", discloses a movable stylet telescopically received in a hollow movable cannula, both the stylet and the cannula being mounted to hubs within a pistol-style grip. In use, the stylet is first manually advanced into the tissue and the cannula is then driven over the stylet by depressing a trigger.

U.S. Pat. No. 4,699,154, issued Oct. 13, 1987 to one Lindgren for "Tissue Sampling Device", discloses a complicated biasing mechanism in which a release button is depressed to cause a spring-loaded stylet to be advanced into the tissue mass. The forward movement of the stylet also triggers the delayed release of a spring-loaded outer cannula, which slides over the stylet to sever the tissue sample.

The aforementioned U.S. Pat. No. 4,600,014 to Beraha discloses an embodiment in which, after a slidable stylet is manually advanced into the tissue mass, a spring-loaded outer cannula is released and driven over the stylet to sever the tissue sample.

Several prior automated biopsy instruments employ a stylet formed with an elongated transverse slot or notch adjacent to its sharpened tip. This slot provides a pocket in which is captured a severed tissue sample when the cannula is driven forward over the stylet in the second step of the biopsy procedure. Typical of this form of stylet is the TRU-CUT ® Needle marketed by Travenol Laboratories, Inc., Deerfield, Ill.

An important feature of another known device, The Roth Biopsy Needle, marketed by Cook Urological, Inc., Spencer, Ind., is a stylet which is manually adjustable between extended and retracted positions for reasons which will be apparent from the following description of its various methods of operation. The stylet is loaded from the rear of the instrument and extends behind the instrument at all times. The stylet is mounted to a U-shaped handle which is engageable with the body of the instrument in two positions corresponding to the extended and retracted stylet positions. A spring-loaded cannula is also movable between a charged or rear position and a discharged or advanced position.

In one method of using the Roth needle, the physician first adjusts the stylet manually to its retracted position and moves the cannula manually to the charged position to expose the sharpened tip of the stylet. He then penetrates the tissue mass with the stylet and depresses a button-release to cause the cannula to be driven by the spring forwardly over the tip of the stylet to sever the tissue sample and retain it within the hollow tip of the cannula. It is to be borne in mind that the stylet of the Roth needle is movable, as mentioned above, and that the button-release is exposed at all times and therefore subject to inadvertent actuation. It should also be noted that because the stylet and the associated U-shaped handle extend behind the instrument, the stylet and handle are always exposed and are therefore vulnerable to accidental impact or unintended forces, thereby creating a risk that the stylet may be inadvertently advanced into the body of the patient with possibly deleterious consequences.

In another method of using the Roth needle, the physician proceeds as before, but after penetrating the tissue mass he manually advances the stylet to its extended position to expose the transverse slot or gap therein described above. When the cannula is advanced, the tissue sample is severed and captured in the pocket formed by the slot.

In an alternative variation of the foregoing method, the physician may begin the procedure with the stylet in the extended position and the cannula in the discharged mode. Once the tissue has been penetrated, the cannula is manually retracted to expose the transverse slot. However, it is to be noted that all stylets formed with such a tissue pocket, whether employed in the Roth needle or in other biopsy instruments, become unstable when tooled to gauge sizes larger than 20 gauge (i.e., 21, 25 gauge). At higher gauge numbers (i.e., smaller diameter stylets) the bridge joining the stylet's proximal and distal ends at the tissue pocket becomes increasingly flexible, and therefore the stylet becomes physically unstable and its direction impossible to control with any precision when the slot or gap is exposed during penetration of the tissue mass by the stylet. Moreover, certain areas of the body such as the pancreas, thyroid, and nonpleural-based intrapulmonary lesions are routinely biopsied with needles smaller than 20 gauge (i.e., 21 gauge) to reduce the incidence of hemorrhage and pneumothorax.

In any event, the various automated biopsy instruments presently known tend to be heavy, difficult to manipulate, and incorporate biasing mechanisms which are either complicated in construction or require undue force to operate. Such limitations diminish the physician's control over the instrument and the precision with which biopsies may be performed. These instruments may be subject to inadvertent movement or torque which may, in turn, subject the patient to unnecessary trauma and risk. This is especially true of instruments which permit or require adjustment of the relative positions of any of their elements before the cannula is moved forward to sever the tissue sample. Similarly, the length of time required to perform a biopsy increases as the physician's degree of control of the instrument decreases, further elevating the risk to which the patient may be exposed. Finally, both physician and patient are exposed to the risk of inadvertent advancement of the cannula when the instrument is in its charged condition.

SUMMARY OF THE INVENTION

The present invention provides a biopsy instrument which comprises stationary means for mounting a stylet on the instrument in fixed relation thereto so that the stylet, once mounted on the instrument, cannot be moved relative thereto, inadvertently or otherwise. A guide means is provided for mounting a cannula on the instrument and is reciprocably movable relative to the stationary means between a charged position, in which the cannula is retracted in a direction away from the distal end of the stylet, and a discharged position, in which the cannula is displaced from the charged position in the direction of the distal end of the stylet. Biasing means such as a coil spring urge the guide means toward the discharged position.

The instrument according to the invention also includes manually operable charging means for moving the guide means to the charged position against the urging of the biasing means, and manually actuable release means for releasably retaining the guide means in the charged position against the urging of the biasing means.

It should be noted at this juncture that the term "distal" is used herein in its ordinary sense to mean "remote from the point of attachment", and that the term "proximal" is used hereinafter in its meaning of "at, adjacent to or near the point of attachment."

In preferred embodiments of the invention, a shield means is provided which is disposed to block or prevent inadvertent actuation of the release means. More particularly, the charging means preferably includes the shield means and is movable between the safety position and a charged-ready position in which the shield means is displaced from the safety position to expose the release means for actuation.

Other features and advantages of the invention will be apparent from the ensuing description in conjunction with the accompanying drawings.

BRIEF DESCRIPTION OF THE DRAWINGS

In the drawings:

FIG. 4 is a longitudinal sectional view similar to FIG. 2 but showing the biopsy instrument of FIGS. 1 to 3 in a "charged-ready" mode;

FIG. 4A is a longitudinal sectional view similar to FIG. 2 but showing the biopsy instrument of FIGS. 1 to 4 in a "discharged" mode;

FIG. 6 is a longitudinal sectional view taken along line 6—6 of FIG. 5A and showing the biopsy instrument of FIGS. 5 and 5A in a "charged-safety-on" mode;

FIG. 7 is a longitudinal sectional view of the biopsy instrument of FIGS. 5, 5A and 6, taken along line 7—7 of FIG. 5A;

FIG. 8 is a longitudinal sectional view similar to FIG. 6 but showing the biopsy instrument of FIGS. 5 to 7 in a "charged-ready" mode;

FIG. 8A is a longitudinal sectional view similar to FIG. 6 but showing the biopsy instrument of FIGS. 5 to 8 in a "discharged" mode.

DETAILED DESCRIPTION OF THE INVENTION

Figure 1:
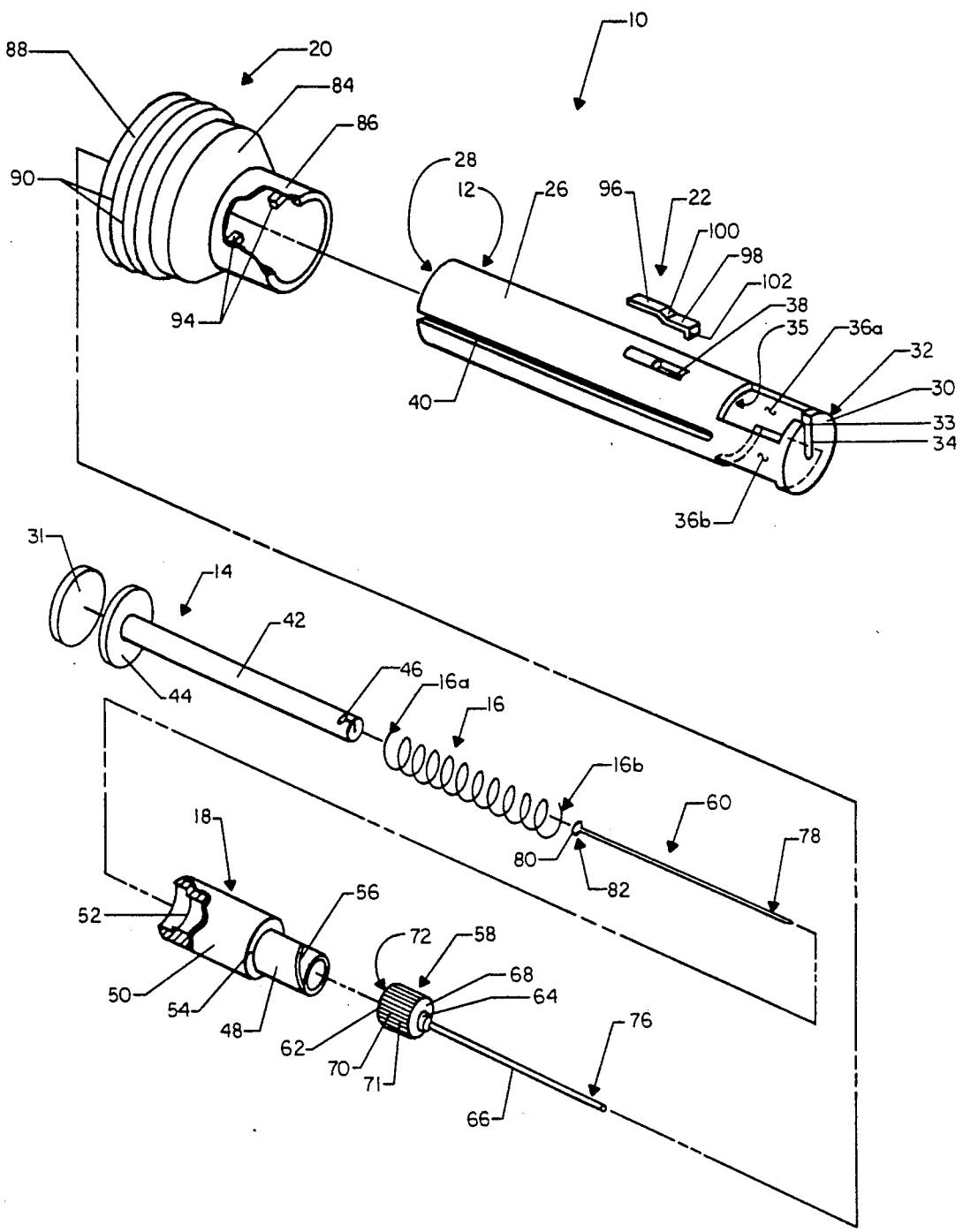
FIG. 1 is an exploded perspective view of the major components of a biopsy instrument comprising an embodiment of the invention.
Figure 1A:
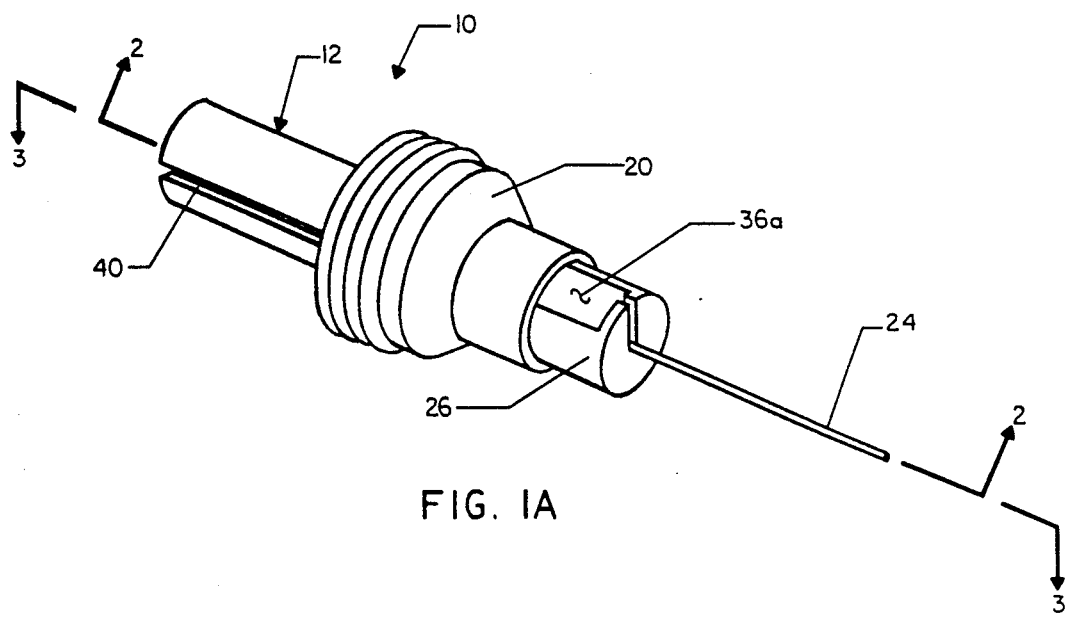
FIG. 1A is a perspective view of the biopsy instrument of FIG. 1 in a fully assembled condition.

Referring now to the drawings, and particularly to FIGS. 1 and 1A, an automated biopsy instrument according to the invention is designated generally by the reference numeral 10. The instrument 10 comprises seven principal elements, which will be more fully described hereinbelow: an outer casing 12; an inner support rod 14; a coil spring 16; a biopsy spring guide 18; a safety cap 20; a release lever 22; and a needle 24.

The outer casing 12 comprises an elongated hollow cylindrical tube 26 open at a rear end 28 thereof and substantially closed by an end wall 30 which is formed integrally with the tube 26 at the opposite or forward end 32 thereof. The open end 28 is closed by a cap 31. A cannula slot 34 in the end wall 30 communicates with a hollow interior 35 of the tube 26. The slot 34 extends radially from a center point of the end wall 30 to the periphery thereof. A cone-shaped depression 34a is formed in the interior face of the end wall 30 at the closed end of the slot 34, the broader end of the depression 34a opening toward the interior 35 of the tube 26.

Provided in the tube 26 at the forward end 32 thereof, and spaced from the end wall 30, are a pair of substantially rectangular access ports 36a and 36b which communicate with the hollow interior 35 of the tube 26. Access port 36a circumscribes an arc of approximately 90 degrees about the circumference of the outer casing 12, communicates with the cannula slot 34 at an intersection designated by the reference character 33, and extends symmetrically in either direction from the intersection 33. Access port 36b is diametrically opposite from port 36a and is identical therewith except that it does not communicate with the cannula slot 34.

The outer casing 12 includes a release lever seat 38 provided by a rectangular aperture which is formed in the tube 26 and communicates with the interior 35 thereof. Seat 38 is positioned approximately at the longitudinally central portion of the tube 26 and in line with the cannula slot 34.

The outer casing 12 is additionally provided with a pair of longitudinal guide slots 40 which are formed in the tube 26 and extend from the rear end 28 thereof toward the opposite or forward end 32. The guide slots 40 are disposed diametrically oppositely from one another and approximately midway between, or 90 degrees from, the access ports 36a, 36b.

The internal support rod 14 comprises an elongated solid cylindrical shaft 42 joined to a circular or disc-shaped base 44. An anchor socket or clevis 46 is formed in the distal end of the shaft.

The biopsy spring guide 18 is hollow and open at its opposite ends and comprises a forward cylinder 48 and a rear cylinder 50 joined coaxially therewith. The outside diameter of the forward cylinder 48 is smaller than that of the rear cylinder 50, the forward cylinder 48 communicating with and extending from the rear cylinder 50. An annular internal shoulder 52 is formed in the rear cylinder 50. The walls of the two cylinders are continuous, thereby forming an annular external shoulder 54. The exterior surface of the distal end of the forward cylinder is formed with a quarter-turn male thread 56.

Figure 2:
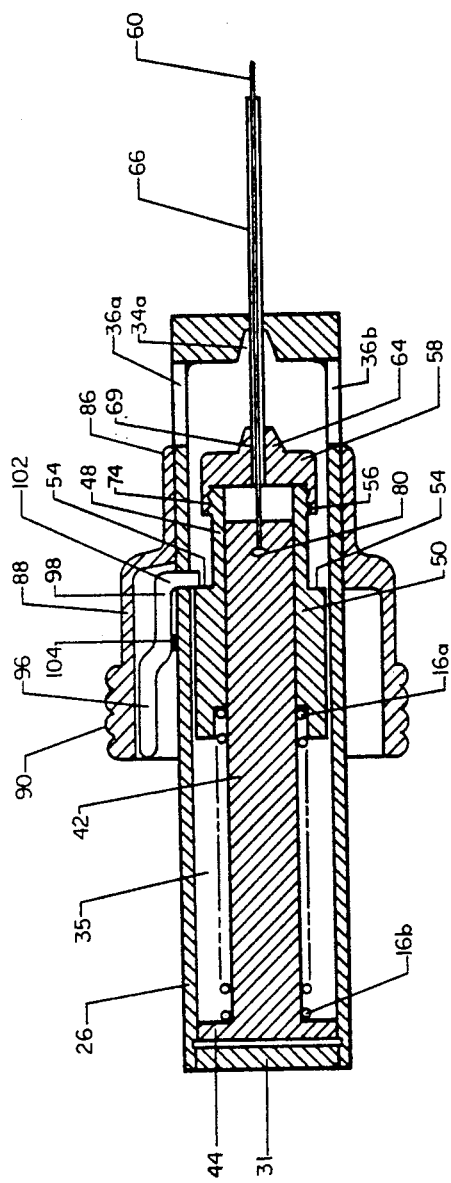
FIG. 2 is a longitudinal sectional view taken along line 2—2 of FIG. 1A and showing the biopsy instrument of FIGS. 1 and 1A in a "charged-safety-on" mode.

The needle 24 comprises a cannula mount 58 and a stylet 60. The cannula mount 58, in turn, comprises a cylindrical collar 62, a conical head 64, and a cutting cannula 66. The collar 62 is open at one end thereof and is closed at its opposite end by an end wall 68 pierced by a centrally disposed, narrow axial bore 69 (FIG. 2). An outer surface 70 of the collar 62 is provided with knurling 71 for improved grip, while an inner surface 72 is formed with a quarter-turn female thread 74 adapted to mate with the thread 56 of spring guide 18. The conical head 64 is secured to the end wall 68 over the axial bore 69, and is itself axially bored to communicate with the interior of the cylindrical collar 62 by way of bore 69, whereby the cutting cannula 66 is received by the head 64 and end wall 68 and is there secured in any suitable manner. The cutting cannula 66 comprises a hollow tube which is beveled to an appropriate angle at its distal end 76 (the particular angle depending on the style of cannula employed) and sharpened about its circumference at the distal end 76.

It will be noted at this point that the hollow interior of the cannula is in communication with the interior of collar 62.

Although the cutting cannula 66 is described as being of a certain configuration, it is not so limited. Because the cannula mount 58 is detachably affixed to the spring guide 18, the biopsy instrument 10 may interchangeably employ a needle having any one of several configurations well known in the art, including but not limited to those variously known by or marketed under the names Turner, Chiba, Franseen, Tip-cut, Menghini, and Bernardino/Sones. The biopsy instrument 10 may also employ a TRU-CUT needle, as discussed more fully hereinafter.

The stylet 60 is sharpened to a point at its distal end 78 and is formed with an anchor 80 at its proximal end 82. It will be apparent that the stylet need not be formed with a tissue pocket or sampling gap; that is, a transverse slot located adjacent to the sharpened distal end 78, as will be discussed with greater particularity hereinafter.

The safety cap 20 or shield means is a roughly bell-shaped hollow element open at both ends and surrounding the cylindrical tube 26. A web 84 thereof joins a narrow, hollow cylindrical forward section 86 to a hollow cylindrical rear section 88 of greater diameter than the forward section 86. The rear section 88 is formed with a series of circumferential ribs 90 for improved grip, and it will be noted that configuration of the safety cap 20 is such that it may be encirclingly engaged or grasped by the thumb and fingers of one hand. Integrally formed on an interior surface 92 of the forward section 86 of the safety cap, at a point where the forward section 86 and the web 84 merge, are a pair of oppositely disposed, elongated guide pins 94 of square cross section.

The release lever 22 comprises a finger rest 96 and a mounting section 98 maintained in spaced parallel planes by a connecting web 100. The finger contacting surface of the finger rest 96 may be appropriately textured for improved grip. Mounting section 98 is formed with a latching projection 102 at one end of the release lever and is flexibly secured to the outer casing 12 by a spot weld 104 (FIG. 2).

In assembly, a biasing means in the form of the coil spring 16 is coaxially received over the cylindrical shaft 42 of the internal support rod 14 with a first end 16a of the spring bearing against the base 44 to which the shaft 42 is mounted. The rod 14 and the spring 16 are in turn telescopically received within the biopsy spring guide 18 with a second or opposite end 16b of the spring 16 bearing against the internal shoulder 52 of the spring guide.

Next, the support rod 14, the coil spring 16, and the spring guide 18 are telescopically received within the outer casing 12, and the subassembly so formed is then received within the safety cap 20 with the guide pins 94 thereof registering with the guide slots 40 in the outer casing 12. The safety cap 20 is slidable over the outer casing 12, the extent of forward movement thereof being limited by the length of the guide slots 40. The rear end 28 of the tube 26 is closed by the cap 31.

The stylet 60 is telescopically or coaxially received within the cannula mount 58 to assemble the needle 24. The needle is then positioned within the hollow interior 35 of the tube 26 with the collar 62 of the cannula mount 58 aligned with the access ports 36a, 36b and the cannula 66 resting in the cannula slot 34. In this position, the anchor 80 of the stylet 60 is received and detachably engaged within the clevis 46 of the spring guide 18. The thread 74 on the inner surface 72 of the collar 62 is engaged with the thread 56 on the spring guide 18 to secure the cannula mount 58 to the spring guide.

The fully assembled biopsy instrument 10 has three operating modes: namely, the discharged mode, the charged-safety-on mode, and the charged-ready mode. In the discharged mode, best shown in FIG. 4A, the safety cap 20 is positioned approximately at the forward end 32 of the tube 26 so that the forward section 84 of the safety cap covers the access ports 36a, 36b. The spring guide 18 is disposed at the forward end 32 of the tube 26 with the head 64 of the cannula mount 58 resting within the complementary cone-shaped depression 34a.

Figure 3:
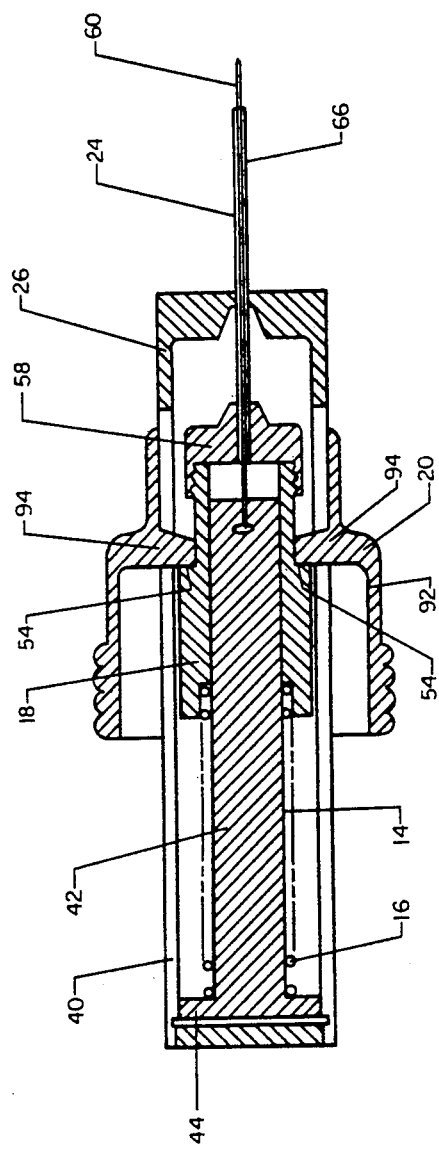
FIG. 3 is a longitudinal sectional view of the biopsy instrument of FIGS. 1, 1A and 2, taken along line 3—3 of FIG. 1A.
Figure 5:
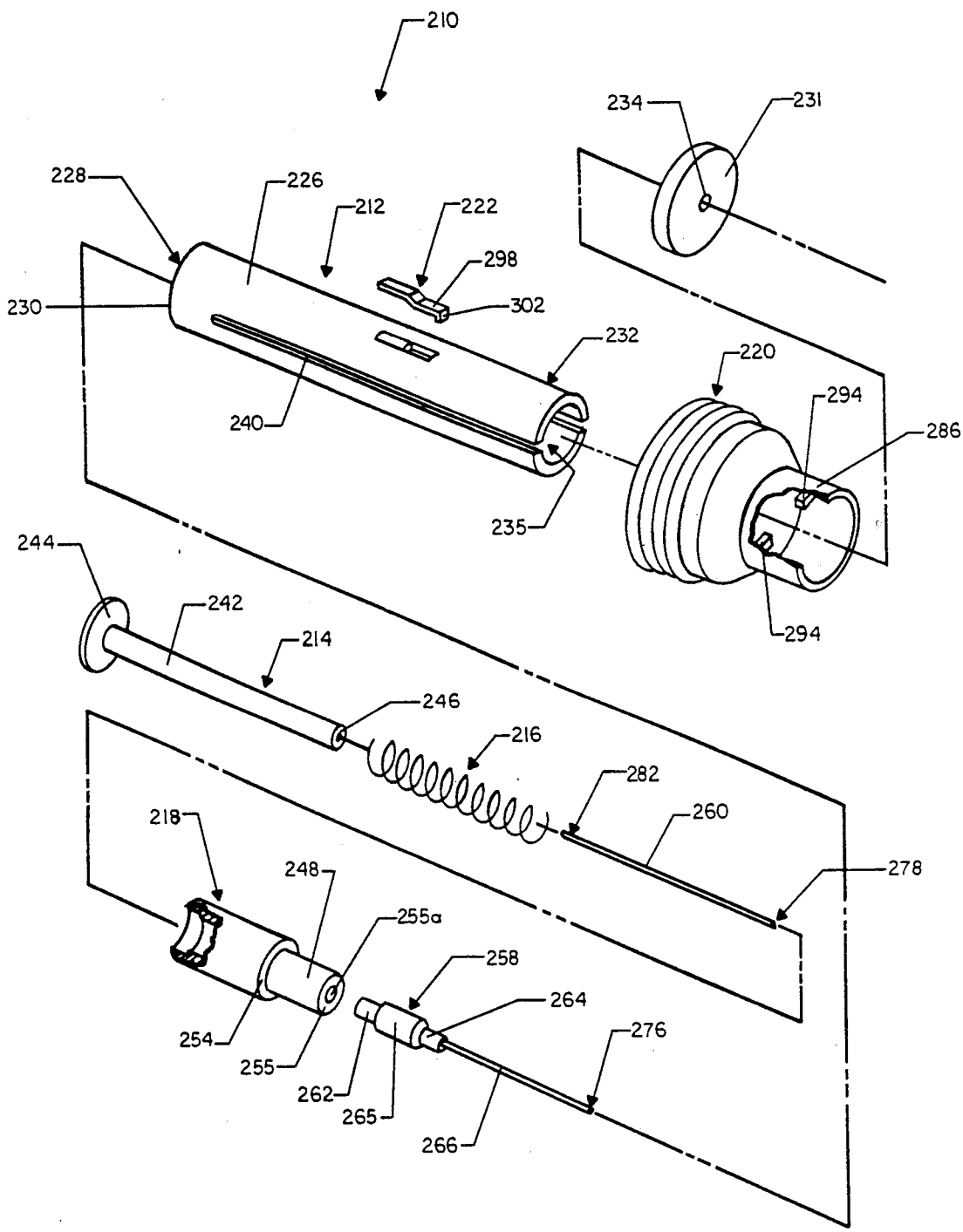
FIG. 5 is an exploded perspective view similar to FIG. 1 but showing a biopsy instrument comprising an alternative embodiment of the invention.

The instrument 10 may be converted from the discharged mode to the charged-safety-on mode, best shown in FIG. 2, by retracting the safety cap 20 toward the rear end 28 of the tube 26. The configuration of the safety cap permits this to be done with equitable distribution of the retracting force applied by the hand of the physician: that is, unlike examples of the prior art, the retracting force is not concentrated at the tip of the thumb or one or two fingers. This action causes the guide pins 94 (FIG. 3) to engage the annular external shoulder 54 of the spring guide 18 to retract the spring guide toward the base 44 of the support rod 14 and compress the coil spring 16. Thus, an easy functioning, manually operated charging means has been provided. At the same time, and by this action, the cannula 66 is retracted to expose the distal end portion of the stylet 60. However, it is important to note that a stationary means for mounting the stylet on the instrument 10 in fixed relation thereto has been provided; both the stylet 60 and the support rod 14 remain stationary. The safety cap 20 and the spring guide 18 are retracted in this manner until the latching projection 102 on the release lever 22 engages the annular external shoulder 54 of the spring guide, as depicted in FIG. 2. In the charged-safety-on mode, the rear section 88 of the safety cap 20 covers the release lever 22 to prevent accidental actuation of the instrument 10.

If the instrument 10 has not yet been used to perform a biopsy, it must now be loaded with a needle 24 while in the charged-safety-on mode. With the access ports 36a, 36b exposed, the biopsy instrument 10 is loaded by registering the anchor 80 on the stylet 60 with the clevis 46. The cannula mount 58, sheathing the stylet 60, is secured to the spring guide 18 by mating the thread 56 on the spring guide 18 with the thread 74 on the inner surface 72 of the collar 62 and executing a quarter-turn to secure the mating engagement of the threads.

To convert the instrument 10 to the charged-ready mode, best shown in FIG. 4, the safety cap 20 is moved forward until the guide pins 94 have traversed the full extent of the guide slots 40 with the safety cap covering the access ports 36a, 36b, as in the discharged mode, and exposing the release lever 22. (Alternatively the safety cap 20 may be formed with a thumb hole, not shown in the drawings, positioned over the release lever 22. In this arrangement the safety cap need not be moved forward to expose the release lever 22 but rather the release lever may be depressed, as described below, by applying sufficient force to the area of the thumb hole to overcome the natural resilience of the material of construction).

The biopsy instrument 10 is now ready for use. To obtain a biopsy, the location of the tissue to be sampled is located by one or more of a variety of methods, such as fluoroscopy, sonography, computed tomography, magnetic resonance imaging, or palpation. With the instrument 10 in the charged-safety-on-mode, the needle 24 is positioned in the tissue to be biopsied. If the operator has not already done so, he slides the safety cap 20 forward and actuates the instrument by depressing the finger rest 96 on the release lever 22, which is flexibly welded to the outer casing 12 as described hereinabove. Manipulation of the release lever raises the latching projection 102, disengaging it from the external shoulder 54 of the spring guide 18.

When the latching projection 102 is disengaged, the stored energy of the biasing means or compressed coil spring 16 is released to drive the cannula 66 forward over the stationary stylet 60 and into the mass. (If the safety cap is formed with a thumb hole, the compressed energy of the coil spring 16 will drive both the cannula and the safety cap forward because the guide pins 94 on the safety cap will be drivingly engaged by the external shoulder 54 of the spring guide 18.) Thus, a guide means for mounting the cannula 66 to the instrument 10 for reciprocating movement relative to the stationary means, between a charged position and a discharged position, has been provided.

This movement of the cannula causes its sharpened distal end 76 to cut and isolate a sample plug or core of tissue from the mass and retain it within the hollow interior of the cannula 66. The instrument 10 is now in the discharged mode (FIG. 4A), as described hereinabove, and the instrument 10 may now be withdrawn from the patient. The biopsy sample is extracted from the cannula by returning the instrument to the charged-safety-on mode, thereby retracting the cutting cannula 66 from over the end of the stylet 60 to eject the sample.

Figure 9:
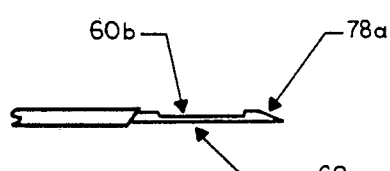
FIG. 9 is a fragmentary view of an alternative form of a stylet for a biopsy instrument according to the invention.

Because the stylet 60 is detachably affixed within the clevis 46, it may be interchanged with an alternative stylet 60a, shown fragmentarily in FIG. 9. The stylet 60a is identical to the stylet 60 except that the overall length of the stylet 60a is approximately one to two centimeters greater than that of the stylet 60, and the stylet 60a is provided with a transverse slot or sampling gap creating a tissue pocket 60b adjacent to the stylet's sharpened distal end 78a. This stylet is substantially similar to the TRU-CUT Needle marketed by Travenol Laboratories of Deerfield, Ill. The stylet 60a may be used to perform the style of biopsy commonly referred to as the TRU-CUT method.

In performing the TRU-CUT method of biopsy using a biopsy instrument according to the present invention, the physician penetrates the mass of tissue to be sampled with the instrument 10 in the discharged mode. Because the stylet 60a is slightly longer than the stylet 60, the distal end 78a of the stylet 60a, unlike the distal end 78 of the stylet 60, projects slightly beyond the distal end of the cutting cannula 66 in the discharged mode. As the second step of the biopsy, the instrument 10 is converted to the charged-safety-on mode by retracting the cannula 66 in the manner described hereinabove. This exposes the tissue pocket 60b of the stylet 60a. In the final step of the biopsy, the physician actuates the instrument 10 by depressing the finger rest 96 of the release lever 22, which permits the energy of the compressed coil spring 16 to drive the cannula 66 forward over the stylet 60a to sever a tissue sample and retain it in the tissue pocket 60b until the instrument can be withdrawn from the patient.

FIGS. 5 to 8A illustrate an alternative embodiment of the invention in the form of a biopsy instrument 210 which is intended to be disposed of after a single use or a limited number of uses during a single procedure (perhaps three to five), whereas the embodiment illustrated in FIGS. 1 to 4A, excluding the needle 24, is suitable to be reused indefinitely. There are small differences between the two embodiments, but basic structure is quite similar in both, and their principles of operation are virtually identical. The following description is directed principally but not exclusively to the differences.

Figure 5A:
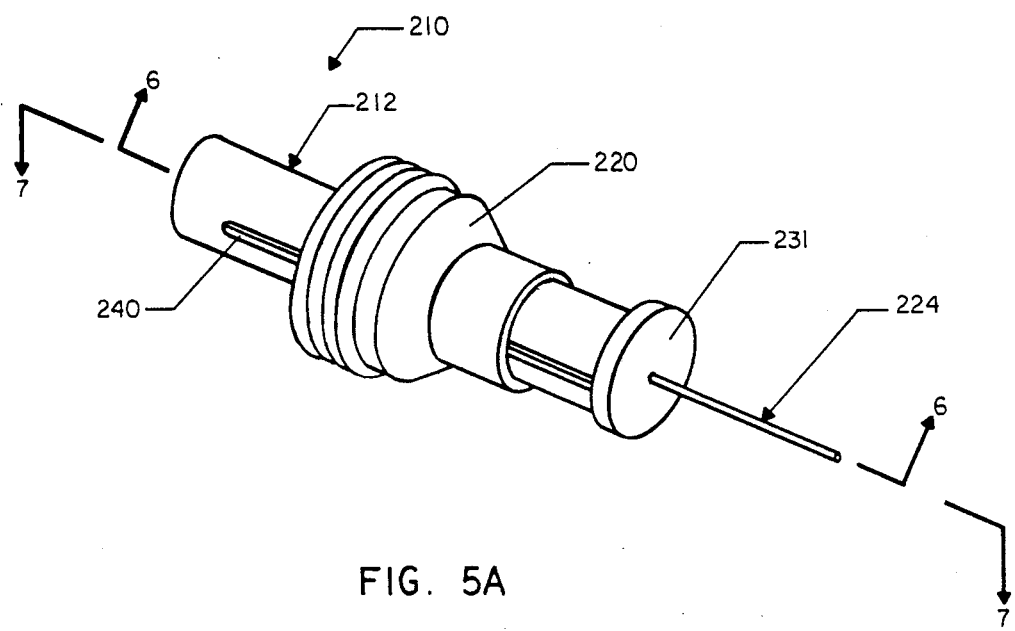
FIG. 5A is a perspective view of the biopsy instrument of FIG. 5 in a fully assembled condition.

In FIGS. 5 to 8, reference numerals are greater by 200 than the respective reference numerals which identify identical or analogous elements or features depicted in FIGS. 1 to 4A. Thus, referring particularly to FIGS. 5 and 5A, an automated biopsy instrument 210 comprises an outer casing 212, an inner support rod 214, a coil spring 216, a biopsy spring guide 218, a safety cap 220, a release lever 222, and a needle 224.

In this embodiment, the cylindrical tube 226 is preferably formed of materials such as polycarbonate, delrin, nylon, polyethylene, polyvinyl chloride, acrylic, or acrylonitrile-butadiene-styrene, and is open at its forward end 232 and closed at its rear end 228 by an end wall 230 formed integrally therewith. A circular cap 231 snap-fits over the tube 226 to close the open forward end 232. A cylindrical depression 234a (FIG. 6) is formed about the center of the interior face of the cap 231. An axial bore 234 through the center of the cap communicates with the depression 234a.

Also in this embodiment, the longitudinal guide slots 240 extend from the forward end 232 of the tube 226 toward the rear end 228, a recess 246 is formed in the distal end of the internal support rod 214, and the forward cylinder 248 is formed with an end wall 255 pierced by a bore 255a.

The cannula mount 258 comprises a narrow base 262, a narrow cylindrical head 264 and a midsection 265 integrally joining the base and the head. The base 262, the head 264, and the midsection 265 are axially bored to receive the cutting cannula 266, which may there be secured by means of adhesive (not shown) and which comprises a hollow cylindrical tube beveled at its distal end 276 to an appropriate angle (the particular angle depending on the style of cannula employed) and sharpened about the circumference of the distal end.

The mounting section 298 of the release lever 222 is flexibly solvent-bonded to the outer casing 212 at 304.

Assembly of instrument 210 is quite similar to assembly of instrument 10, as described hereinabove. However, in this instance, the proximal end 282 of the stylet 262 is adhesively bonded within the recess 246, and the base 262 of the cannula mount 258 is similarly secured within the bore 255a.

In any event, the internal support rod 214, the coil spring 216, the spring guide 218, and the needle 224 are telescopically received within the safety cap 220 and the outer casing 212, the guide pins 294 being received in the guide slots 240, and the cutting cannula 266 and the stylet 260 being received in the axial bore 234. The safety cap 220 is now slidable over the outer casing 212, the extent of forward movement being limited by the cap 231 which is applied to the tube 226 to close the forward end 232 thereof as well as the open ends of the guide slots 240.

Like the instrument 10, the assembled biopsy instrument 210 is operated in a discharged mode, a charged-safety-on mode, and a charged-ready mode. In the discharged mode (FIG. 8A), the safety cap 220 is positioned near the forward end 232 of the tube 226 in engagement with the cap 231. The spring guide 218 is also disposed near the forward end of the tube 226 with the cylindrical head 264 of the cannula mount 258 resting within the complementary cylindrical depression 234a.

The instrument 210 is converted to the charged-safety-on mode (FIG. 6) by retracting the safety cap 220 toward the rear end 228 of the outer casing 212, causing the guide pins 294 to engage the external shoulder 254 of the spring guide 218 and thus retract the spring guide toward the base 244 of the support rod 214 and compress the spring 216 (FIG. 7). The cannula 266 is simultaneously retracted to expose the distal end 278 of the stylet 260, both the stylet 260 and the support rod 214 remaining stationary, and the latching projection 302 of the release lever 222 engages the external shoulder 254 of the biopsy spring guide 218. In the charged-safety-on mode, the rear section 288 of the safety cap 220 conceals the release lever 222 to prevent accidental actuation of the biopsy instrument 210.

In converting to the charged-ready mode (FIG. 8), the safety cap 220 is slid forward into engagement with the cap 231, as in the discharged position, thereby exposing the release lever 222. The instrument 210 is now ready to be used to obtain a tissue sample in precisely the same procedure described above in connection with instrument 10 (and alternatively, the safety cap 220 may be formed with a thumb hole as described hereinabove in connection with the embodiment of FIGS. 1 to 4A). Also similar to the embodiment of FIGS. 1 to 4A, the instrument 210 may be provided with the stylet 60a, shown fragmentarily in FIG. 9, to replace the stylet 260. In the event the stylet 260 is replaced by the stylet 60a, the distal end 78a of the stylet 60a projects slightly beyond the distal end of the cannula 266 in the discharged mode, as described hereinabove.

The materials from which certain biopsy instruments according to the invention are constructed may be selected so that the instruments will be suitable for use in conjunction with magnetic resonance imaging (MRI), a medical examination technique which requires the use of instruments comprised entirely of nonferromagnetic materials. Thus, the stylets 60 and 260 and the cutting cannulas 66 and 266, which are otherwise preferably formed of a suitable grade of stainless steel, would be replaced by stylets and cutting cannulas formed of nonferromagnetic metals typically having a high nickel content. The coil spring 16 or 216, also normally formed of steel, would be replaced by a spring formed from an alternative material having appropriate resilience and shape-retention characteristics, such as a nonferromagnetic metal having a high nickel content or the synthetic resinous material marketed by E. I. du Pont de Nemours & Co. of Wilmington, Del. under the name Hytrel.

Each of the embodiments disclosed herein may be used in conjunction with an outer guide cannula (not shown in the drawings) for performing multiple, successive biopsies on the same patient, although it should be understood that the outer guide cannula is not necessary for practicing the invention. The outer guide cannula is an elongated narrow cylindrical tube open at both ends and telescopically receivable over the needle 24, 224. It is inserted in the incision made in the tissue mass during the biopsy. If a subsequent biopsy of the same region of tissue is called for, the outer guide cannula may be allowed to remain in place in the incision when the biopsy instrument is removed to retrieve the tissue sample from the previous biopsy. To perform subsequent biopsies, the instrument is used as described hereinabove but the needle is inserted into the outer guide cannula to be conducted thereby to the correct location to perform each subsequent biopsy. This eliminates any need to leave the entire instrument projecting from the body of a patient while the tissue sample is retrieved, as must be done in such procedures when using certain known biopsy instruments from which the stylet must be removed in order to retrieve the sample.

Under either of the styles of biopsy and using either of the embodiments described hereinabove, an easily manipulated and manually compatible instrument 10, 210 is provided. The outer casing 12, 212 is of a size, shape and weight such that it can be readily held and gripped by a single hand. Further, the instrument 10, 210 is easily converted from the discharged to the charged mode by retracting the safety cap 20, 220 and the spring guide 18, 218. The pair of guide pins 94, 294 equitably distribute the force of retraction about the circumference of the annular external shoulder 54, 254 of the spring guide 218 thereby enabling the physician to readily charge the instrument. The safety cap 20, 220 provides an important degree of protection for the patient. The physician must manually advance the safety cap 20, 220 forward to expose the release lever 22, 222 or, alternatively, must supply sufficient force to the area defining the thumb hole to overcome the natural resilience of the material comprising the safety cap to depress the release lever 22, 222. In either event, the likelihood that the instrument 10, 210 may be accidentally actuated has been substantially reduced. The compact size and shape of the instrument 10, 210 affords the physician great control over the operation and manipulation of the same. Thus, the patient is less likely to sustain serious injury which could result from unwanted instrument movement or torque.

While the invention has been particularly described in connection with certain specific embodiments thereof, it is to be understood that this is by way of illustration and not of limitation, and the scope of the appended claims should be construed as broadly as the prior art will permit.

What is claimed is:

1. A biopsy instrument comprising an elongate hollow casing, a needle extending outwardly from the casing and having a cannula and a stylet received within the cannula, a stationary support mounted within the casing in fixed relation thereto and having means affixing the stylet thereto, a guide having means affixing the cannula thereto and being carried within the casing for reciprocating movement relative to the stationary support between a charged position, wherein the cannula is retracted in a direction away from the distal end of the stylet, and a discharged position, wherein the cannula is displaced from the charged position in the direction of the distal end of the stylet, relative to the charged position, a coil spring engaged between the stationary support and the guide to urge the guide toward the discharged position, a manually operable charging member surrounding the casing and being mounted thereon for reciprocal sliding movement relative thereto, the charging member having means engageable with the guide to move the guide to the charged position against the urging of the spring, and a release lever having means engageable with the guide for retaining the guide in the charged position, the release lever being manually actuable from without the casing to release the guide for movement to the discharged position.

2. A biopsy instrument according to claim 1, wherein the longitudinal axis of the casing is common to the stylet, the cannula, the stationary support, the guide, the spring, and the charging member, the release lever being supported on the casing in a disposition offset from said longitudinal axis.

3. Support means for a biopsy needle having a cannula and a stylet coaxially receivable within the cannula, the support means comprising a casing, stationary means on the casing for mounting a stylet thereto in fixed relation therewith, guide means carried by the casing for mounting a cannula thereto with the stylet received coaxially within the cannula, the guide means being reciprocally movable relative to the stationary means between a charged position, wherein the cannula is retracted in a direction away from the distal end of the stylet, and a discharged position, wherein the cannula is displaced from the charged position in the direction of the distal end of the stylet, biasing means carried by the casing for urging the guide means toward the discharged position, charging means mounted on the casing, the charging means being manually operable to move the guide means to the charged position against the urging of the biasing means, and manually actuable release means mounted on the casing and adapted to releasably retain the guide means in the charged position against the urging of the biasing means, the guide means comprising a forward cylinder and a rear cylinder formed coaxially therewith and having a greater diameter, the walls of the two cylinders being joined to form an annular external shoulder engageable by the charging means and by the release means, the forward cylinder having means for mounting the cannula thereto.

4. Support means according to claim 3, wherein the stationary means includes a fixed shaft having a forward end provided with means for mounting the stylet, the rear cylinder of the guide means being slidably received over the forward end of the shaft.

5. A biopsy instrument comprising an elongate hollow casing, a needle extending outwardly from the casing and having a cannula and a stylet received within the cannula, a stationary support mounted within the casing in fixed relation thereto and having means affixing the stylet thereto, a guide having means affixing the cannula thereto and being carried within the casing for reciprocating movement relative to the stationary support between a charged position, wherein the cannula is retracted in a direction away from the distal end of the stylet, and a discharged position, wherein the cannula is displaced from the charged position in the direction of the distal end of the stylet, biasing means for urging the guide toward the discharged position, a manually operable charging member for moving the guide to the charged position against the urging of the biasing means, and a release means for retaining the guide in the charged position, the charging member comprising a safety cap means for blocking inadvertent actuation of the release lever.

6. A biopsy instrument according to claim 5, wherein the charging member is movable to and from a safety position covering the release means.

7. A biopsy instrument comprising an elongate hollow casing, a needle extending outwardly from the casing and having a cannula and a stylet received within the cannula, a stationary support mounted within the casing in fixed relation thereto and having means affixing the stylet thereto, a cannula guide, a cannula mount affixing the cannula to the guide, the guide being completely enclosed by the casing for reciprocating movement therewithin relative to the stationary support between a charged position, wherein the cannula is retracted in a direction away from the distal end of the stylet, and a discharged position, wherein the cannula is displaced from the charged position in the direction of the distal end of the stylet, a coil spring engaged between the stationary support and the guide for urging the guide toward the discharged position, a manually operable charging member for moving the guide to the charged position against the urging of the coil spring, and a release means for retaining the guide in the charged position.

8. A biopsy instrument comprising an elongate hollow casing, a needle extending outwardly from the casing and having a cannula and a stylet received within the cannula, a stationary support mounted within the casing in fixed relation thereto and having means affixing the stylet thereto, a guide having means affixing the cannula thereto and being carried within the casing for reciprocating movement relative to the stationary support between a charged position, wherein the cannula is retracted in a direction away from the distal end of the stylet, and a discharged position, wherein the cannula is displaced from the charged position in the direction of the distal end of the stylet, biasing means for urging the guide toward the discharged position, a manually operable charging member surrounding the casing and being mounted thereon for reciprocal sliding movement relative thereto for moving the guide to the charged position against the urging of the biasing means, and a release means for retaining the guide in the charged position.

9. A biopsy instrument according to claim 8, wherein the casing is provided with longitudinally extending slot means and the charging member is provided with means extending therefrom internally of the casing by way of the slot means engageable with the guide.

10. Support means for a biopsy needle having a cannula and a stylet coaxially receivable within the cannula, the support means comprising a casing, stationary means on the casing for mounting a stylet thereto in fixed relation therewith, guide means carried by the casing for mounting a cannula thereto with the stylet received coaxially within the cannula, the guide means being reciprocally movable relative to the stationary means between a charged position, wherein the cannula is retracted in a direction away from the distal end of the stylet, and a discharged position, wherein the cannula is displaced from the charged position in the direction of the distal end of the stylet, biasing means carried by the casing for urging the guide means toward the discharged position, charging means mounted on the casing, the charging means being manually operable to move the guide means to the charged position against the urging of the biasing means, and manually actuable release means mounted on the casing and adapted to releasably retain the guide means in the charged position against the urging of the biasing means, the charging means including shield means and being movable relative to the casing between a safety position, wherein the shield means is disposed to prevent inadvertent actuation of the release means, and a second position displaced from the safety position to expose the release means for manual actuation thereof.

11. Support means for a biopsy needle having a cannula and a stylet coaxially receivable within the cannula, the support means comprising a pair of support members for respectively supporting the stylet and the cannula and movable relative to each other between a charged condition and a discharged condition, one of the support members comprising an elongate hollow casing having a rear closed end and a forward closed end spaced from the rear closed end at a fixed distance therefrom, a cannula opening defined in the forward closed end, and stationary means within the casing for mounting a stylet in fixed relation to the casing, the other of the support members comprising guide means enclosed within the casing for mounting a cannula thereto with the cannula extending longitudinally outwardly of the casing by way of the cannula opening and with the stylet received coaxially within the cannula, the guide means being longitudinally reciprocable within the casing relative to the stationary means between a first position corresponding to the charged condition, wherein the cannula is retracted in a direction away from the distal end of the stylet, and a second position corresponding to the discharged condition, wherein the cannula is displaced from the first position in the direction of the distal end of the stylet, biasing means for urging the guide means toward the second position, charging means carried by the casing outwardly thereof and manually movable relative to the casing to move the guide means to the first position against the urging of the biasing means, and manually actuable release means provided at a fixed position on the casing outwardly thereof and engageable with the guide means to releasably retain the guide means in the first position against the urging of the biasing means.

* * * * *

UNITED STATES PATENT AND TRADEMARK OFFICE
CERTIFICATE OF CORRECTION

PATENT NO. : 5,025,797

DATED : June 25,1991

INVENTOR(S) : GREGORY W. BARAN

It is certified that error appears in the above-identified patent and that said Letters Patent is hereby corrected as shown below:

Col. 12, claim 5, line 48, delete "a".

Col. 12, claim 5, line 50, delete "lever" and substitute therefor --means--.

Signed and Sealed this

Twenty-seventh Day of October, 1992

Attest:

DOUGLAS B. COMER

Attesting Officer

Acting Commissioner of Patents and Trademarks